US012134600B2

(12) United States Patent
Machida et al.

(10) Patent No.: US 12,134,600 B2
(45) Date of Patent: Nov. 5, 2024

(54) METHOD FOR PRODUCING A VADADUSTAT INTERMEDIATE

(71) Applicant: KANEKA CORPORATION, Osaka (JP)

(72) Inventors: Koji Machida, Takasago (JP); Hiroaki Yasukouchi, Takasago (JP); Akira Nishiyama, Takasago (JP)

(73) Assignee: KANEKA CORPORATION, Osaka (JP)

( * ) Notice: Subject to any disclaimer, the term of this patent is extended or adjusted under 35 U.S.C. 154(b) by 624 days.

(21) Appl. No.: 17/605,408

(22) PCT Filed: Mar. 5, 2020

(86) PCT No.: PCT/JP2020/009453
§ 371 (c)(1),
(2) Date: Oct. 21, 2021

(87) PCT Pub. No.: WO2020/217733
PCT Pub. Date: Oct. 29, 2020

(65) Prior Publication Data
US 2022/0204451 A1 Jun. 30, 2022

(30) Foreign Application Priority Data
Apr. 26, 2019 (JP) ................ 2019-086759

(51) Int. Cl.
*C07D 213/81* (2006.01)
(52) U.S. Cl.
CPC ................ *C07D 213/81* (2013.01)
(58) Field of Classification Search
CPC .................................. C07D 213/81
USPC ....................................... 546/298
See application file for complete search history.

(56) References Cited

U.S. PATENT DOCUMENTS

| | | |
|---|---|---|
| 2007/0299086 A1 | 12/2007 | Kawamoto |
| 2010/0331303 A1 | 12/2010 | Kawamoto et al. |
| 2010/0331374 A1 | 12/2010 | Wu et al. |
| 2012/0035407 A1 | 2/2012 | Charrier et al. |
| 2012/0309977 A1 | 12/2012 | Lanthier et al. |
| 2013/0203816 A1 | 8/2013 | Kawamoto et al. |
| 2013/0245076 A1 | 9/2013 | Kawamoto et al. |
| 2014/0045899 A1 | 2/2014 | Kawamoto et al. |
| 2014/0057892 A1 | 2/2014 | Kawamoto et al. |
| 2015/0119425 A1 | 4/2015 | Kawamoto et al. |
| 2015/0361043 A1 | 12/2015 | Lanthier et al. |
| 2016/0009648 A1 | 1/2016 | Kawamoto et al. |
| 2017/0189387 A1 | 7/2017 | Kawamoto et al. |
| 2017/0362178 A1 | 12/2017 | Lanthier et al. |
| 2019/0192494 A1 | 6/2019 | Kawamoto et al. |
| 2019/0375713 A1 | 12/2019 | Lanthier et al. |
| 2021/0122715 A1 | 4/2021 | Lanthier et al. |
| 2021/0137901 A1 | 5/2021 | Kawamoto et al. |

FOREIGN PATENT DOCUMENTS

| | | |
|---|---|---|
| CN | 105837502 A | 8/2016 |
| JP | 2009-541486 A | 11/2009 |
| JP | 2013-526539 A | 6/2013 |
| JP | 2014-522409 A | 9/2014 |

OTHER PUBLICATIONS

International Search Report, issued in PCT/JP2020/009453, PCT/ISA/210, dated Apr. 21, 2020.
Qu et al., "Palladium-catalyzed aminocarbonylation of heteroaryl halides using di-tert-butylphosphinoferrocene", Tetrahedron Letters, 2009, vol. 50, p. 6126-6129.
Written Opinion of the International Searching Authority, issued in PCT/JP2020/009453, PCT/ISA/237, dated Apr. 21, 2020.

*Primary Examiner* — Taofiq A Solola
(74) *Attorney, Agent, or Firm* — Birch, Stewart, Kolasch & Birch, LLP

(57) ABSTRACT

A method for producing a first vadadustat intermediate represented by the following formula (3) comprising reacting a compound represented by the following formula (1) with glycine or a glycine derivative represented by the following formula (2) or a salt of the glycine or the glycine derivative in the presence of carbon monoxide.

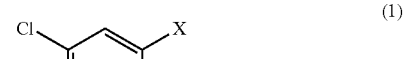

(1)

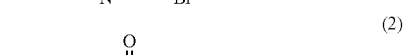

(2)

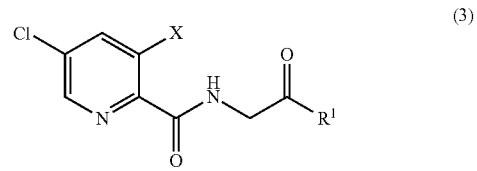

(3)

The method produces a vadadustat intermediate through a clean reaction with high atom conversion efficiency.

9 Claims, 1 Drawing Sheet

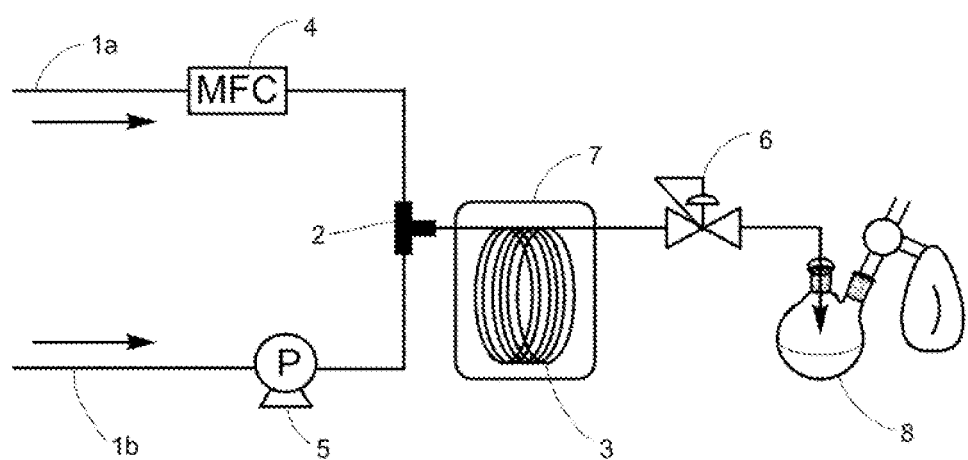

METHOD FOR PRODUCING A VADADUSTAT INTERMEDIATE

TECHNICAL FIELD

The present invention relates to a method for producing a vadadustat intermediate.

BACKGROUND ART

Vadadustat is an oral therapeutic drug for anemia (renal anemia) associated with chronic kidney disease, and is a next-generation oral therapeutic drug that is expected to be applied to a patient refractory to existing an injectable solution (erythropoiesis stimulating agent) (Patent Documents 1 and 2). However, the methods for producing vadadustat disclosed in Patent Documents 1 and 2 require multiple reaction steps (5 to 7 steps) and complicated operation, and their total yields are as low as 9 to 56%.

The method for producing vadadustat including the following steps disclosed in Patent Document 3 shows that the number of reaction steps is reduced to 4 steps and the total yield is improved to 57 to 63% by using 3,5-dichloro-2-pyridinecarboxylic acid and glycine methyl ester hydrochloride as reaction starting materials.

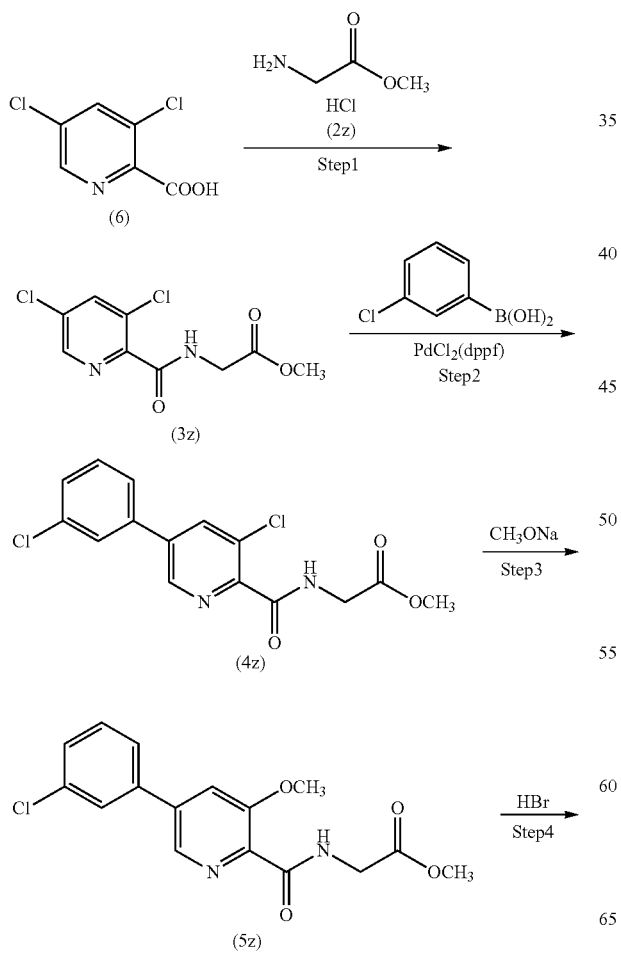

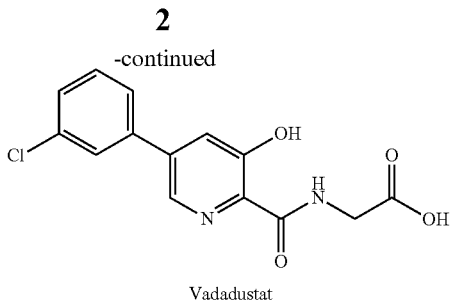

Vadadustat

RELATED ART DOCUMENTS

Patent Documents

Patent Document 1: JP 2009-541486 (A)
Patent Document 2: JP 2014-522409 (A)
Patent Document 3: CN 105837502 (A)

SUMMARY OF THE INVENTION

Problems to be Solved by the Invention

However, in the method for producing vadadustat disclosed in Patent Document 3, a condensation agent such as N,N'-carbonyldiimidazole is used in the first step of synthesizing N-(3,5-dichloropyridine-2-carbonyl)glycine methyl ester (3z) to cause a condensation reaction between 3,5-dichloro-2-pyridinecarboxylic acid (6) and glycine methyl ester hydrochloride (2z). This reaction had low atom conversion efficiency and was not clean. In addition, before proceeding to the reaction of the second step, such after-treatment as extracting and concentrating N-(3,5-dichloropyridine-2-carbonyl)glycine methyl ester (3z) from the reaction solution of the first step was required.

An object of the present invention is to provide a method for producing a vadadustat intermediate through a clean reaction with high atom conversion efficiency.

Solutions to the Problems

The present invention which can solve the problem above-described is as follows.

[1] A method for producing a first vadadustat intermediate comprising:
reacting a compound represented by the following formula (1):

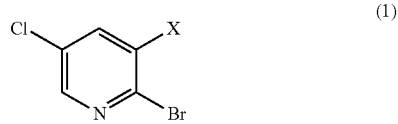

wherein X represents a chlorine atom, a hydroxy group, or OP$^1$; and P$^1$ represents an oxygen protecting group, with glycerine or a glycine derivative represented by the following formula (2):

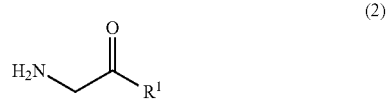

wherein $R^1$ represents a hydroxy group, $OR^2$, or $NR^3R^4$; $R^2$, $R^3$, and $R^4$ independently represent an alkyl group having 1 to 20 carbon atoms and optionally having a substituent, an aryl group having 6 to 20 carbon atoms and optionally having a substituent, or an aralkyl group having 7 to 20 carbon atoms and optionally having a substituent; and $R^3$ and $R^4$ may join together to form a ring, or a salt of the glycine or the glycine derivative in the presence of carbon monoxide to produce the first vadadustat intermediate represented by the following formula (3):

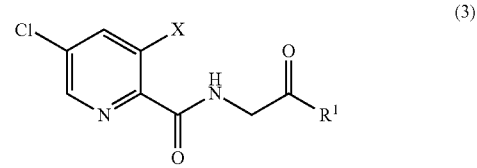

(3)

wherein $R^1$ and X are the same as the above.

[2] The method for producing the first vadadustat intermediate according to [1], wherein the reaction of the compound represented by the formula (1) with the glycine or the glycine derivative represented by the formula (2), or the salt of the glycine or the glycine derivative is performed in the presence of a metal catalyst.

[3] The method for producing the first vadadustat intermediate according to [2], wherein the metal catalyst is a catalyst containing Pd.

[4] The method for producing the first vadadustat intermediate according to any one of [1] to [3], wherein the reaction of the compound represented by the formula (1) with the glycine or the glycine derivative represented by the formula (2), or the salt of the glycine or the glycine derivative is performed in a flow reactor.

[5] The method for producing the first vadadustat intermediate according to [4], wherein the reaction in the flow reactor is performed at 60° C. or higher.

[6] The method for producing the first vadadustat intermediate according to [4] or [5], wherein the reaction in the flow reactor is performed under a pressurized condition of a gauge pressure of 0.1 MPa or more.

[7] The method for producing the first vadadustat intermediate according to any one of [4] to [6], wherein, in the reaction performed in the flow reactor, the amount of the metal catalyst used is 0.05 mol or less per mole of the compound represented by the formula (1).

[8] A method for producing a second vadadustat intermediate comprising:

producing the first vadadustat intermediate represented by the formula (3) by the method according to any one of [1] to [7]; and reacting, subsequently without aftertreatment, a reaction solution containing the obtained first vadadustat intermediate with 3-chlorophenylboronic acid to produce the second vadadustat intermediate represented by the following formula (4):

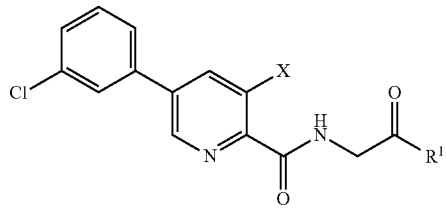

(4)

wherein $R^1$ and X are the same as the above.

Effects of the Invention

According to the present invention, a vadadustat intermediate can be produced through a clean reaction with high atom conversion efficiency.

BRIEF DESCRIPTION OF THE DRAWING

The FIGURE is a schematic view showing an example of the configuration of a flow reactor used in the present invention.

MODE FOR CARRYING OUT THE INVENTION

The present invention is characterized by reacting a compound represented by the formula (1) (hereinafter, may be referred to as the "compound (1)") with glycine or a glycine derivative represented by the formula (2), or a salt of the glycine or the glycine derivative (hereinafter, may be collectively referred to as the "compound (2)") in the presence of carbon monoxide to synthesize a first vadadustat intermediate represented by the formula (3) (hereinafter, may be referred to as the "vadadustat intermediate (3)"). According to the present invention having such characteristics, the vadadustat intermediate (3) can be obtained through a clean reaction with high atom conversion efficiency. Further, even if a reaction solution containing the vadadustat intermediate (3) is, without being subjected to aftertreatment (purification or the like) such as extraction, subsequently reacted with 3-chlorophenylboronic acid, a second vadadustat intermediate represented by the formula (4) (hereinafter, may be referred to as the "vadadustat intermediate (4)") can be efficiently obtained.

Compound (1)

One of starting materials for producing the vadadustat intermediate (3) is a compound represented by the following formula (1):

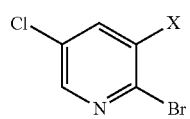

(1)

wherein X represents a chlorine atom, a hydroxy group, or $OP^1$; and $P^1$ represents an oxygen protecting group.

The oxygen protecting group represented by the above $P^1$ (also referred to as a hydroxy protecting group) is not particularly limited, and examples thereof include all groups that can be usually used as a protecting group for an oxygen atom. For example, the oxygen protecting group can be selected from any protecting groups described in PROTECTIVE GROUPS IN ORGANIC SYNTHESIS 4th Edition, JOHN WILEY & SONS Publishing (2007). Specific examples thereof include an alkyl group having 1 to 6 carbon atoms, an aralkyl group having 7 to 12 carbon atoms, an alkoxyalkyl group having 2 to 12 carbon atoms, an acyl group having 1 to 6 carbon atoms, an alkoxycarbonyl group having 1 to 6 carbon atoms, an alkylsulfonyl group having 1 to 6 carbon atoms, an arylsulfonyl group having 6 to 12 carbon atoms, a silyl group, a tetrahydrofuranyl group, and a tetrahydropyranyl group.

The compound (1) is preferably a compound of the formula (1) in which X is a hydroxy group or $OP^1$. When the vadadustat intermediate (3) is produced using a compound of the formula (1) in which X is a hydroxy group or $OP^1$, one (Step 3 in the above formula) of the reaction steps is eliminated, leading to improvement of the production efficiency of vadadustat. From the viewpoint of ease of availability, a compound of the formula (1) in which X is a chlorine atom is particularly preferable.

Compound (2)

One of starting materials for producing the vadadustat intermediate (3) is glycine or a glycine derivative represented by the formula (2):

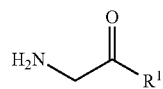

(2)

wherein $R^1$ represents a hydroxy group, $OR^2$, or $NR^3R^4$; $R^2$, $R^3$, and $R^4$ independently represent an alkyl group having 1 to 20 carbon atoms and optionally having a substituent, an aryl group having 6 to 20 carbon atoms and optionally having a substituent, or an aralkyl group having 7 to 20 carbon atoms and optionally having a substituent; and $R^3$ and $R^4$ may join together to form a ring, or a salt of the glycine or the glycine derivative.

Examples of the alkyl group having 1 to 20 carbon atoms represented by $R^2$, $R^3$, and $R^4$ include a methyl group, an ethyl group, a n-propyl group, an isopropyl group, a n-butyl group, and a tert-butyl group.

Examples of the aryl group having 6 to 20 carbon atoms represented by $R^2$, $R^3$, and $R^4$ include a phenyl group, a naphthyl group, and a biphenyl group.

Examples of the aralkyl group having 7 to 20 carbon atoms represented by $R^2$, $R^3$, and $R^4$ include a benzyl group, a phenylethyl group, an a phenylpropyl group.

Examples of the substituent that the alkyl group represented by $R^2$, $R^3$, and $R^4$ optionally has include a halogen atom such as a fluorine atom, a chlorine atom, a bromine atom, and an iodine atom. Examples of the substituent that the aryl group or the aralkyl group represented by $R^2$, $R^3$, and $R^4$ optionally has include a fluorine atom and a chlorine atom. The alkyl group, the aryl group, and the aralkyl group represented by $R^2$, $R^3$, and $R^4$ preferably have no substituent.

Examples of $NR^3R^4$ when $R^3$ and $R^4$ join together to form a ring include a nitrogen-containing ring such as a pyrrolidine ring or a piperidine ring, and a nitrogen-containing ring having 2 to 10 carbon atoms is preferable.

$R^2$ is preferably an alkyl group having 1 to 15 carbon atoms, more preferably an alkyl group having 1 to 10 carbon atoms, further preferably an alkyl group having 1 to 5 carbon atoms, and particularly preferably a methyl group.

$R^3$ and $R^4$ are preferably an alkyl group having 1 to 15 carbon atoms, and more preferably an alkyl group having 1 to 10 carbon atoms.

$R^1$ is preferably a hydroxy group or $OR^2$, and more preferably $OR^2$.

As the salt of the compound (2), inorganic acid salts such as hydrochloride, hydrobromide and sulfate, and organic acid salts such as methanesulfonate can be mentioned, and inorganic acid salts are preferable.

In a reaction by which the vadadustat intermediate (3) is produced from the compound (1) and the compound (2) in the presence of carbon monoxide (hereinafter, may be referred to as the "synthesis reaction of the vadadustat intermediate (3)"), the amount of the compound (2) used is, for example, preferably 0.7 mol or more, more preferably 0.9 mol or more, and further preferably 1.0 mol or more per mole of the compound (1). The upper limit thereof is not particularly limited, and is preferably 4.0 mol or less, more preferably 3.0 mol or less, and further preferably 2.0 mol or less. Hereinafter, the substance amount of the compound (2) per mole of the compound (1) may be referred to as "equivalent (eq)".

Carbon Monoxide

Carbon monoxide is introduced as a gas. In the case of a reaction using a solvent, the reaction is performed in a gas-liquid two-phase system. Carbon monoxide may be introduced alone into a reaction system, or may be introduced into a reaction system in the form of a mixed gas with an inert gas (nitrogen gas, argon gas, or the like). When a reaction is performed using a flow reactor described later, the higher concentration of carbon monoxide in a gas introduced into the reaction system (also referred to as a feed gas) is more preferable, and carbon monoxide is particularly preferably introduced alone. By introducing carbon monoxide with a high concentration, the required amount of carbon monoxide can be fed. The partial pressure ($P_1$) of carbon monoxide in the feed gas is, for example, 50% or more, preferably 80% or more, more preferably 90% or more, and most preferably 100% with respect to 100% of the total pressure ($P_2$).

The carbon monoxide fed to the reaction system as a gas may be carbon monoxide enclosed in a cylinder (specifically, carbon monoxide having a purity of 99% or more and a gauge pressure of about 20 MPa or less), or may be carbon monoxide generated in-line. The method of generating carbon monoxide in-line is not particularly limited, and examples thereof include a method of reacting $(COCl)_2$ with NaOH disclosed in Reaction Chemistry & Engineering, 2016, Vol. 1, pp 280 to 287, and a method of reacting HCOOH with $H_2SO_4$ disclosed in ORGANIC LETTERS, 2013, Vol 15, No 11, pp 2794 to 2797.

Metal Catalyst

The synthesis reaction of the vadadustat intermediate (3) is preferably performed in the presence of a metal catalyst in order to further accelerate the reaction.

Examples of the metal catalyst include metal catalysts containing Ru, Rh, Pt, Pd, Ir, or the like, and a catalyst containing Pd (Pd catalyst or the like) is preferable.

Examples of the Pd catalyst include Pd(PPh$_3$)$_4$(Tetrakis (triphenylphosphine)palladium(0)), Pd(dba)$_2$(Bis(dibenzylideneacetone)palladium(0)), Pd$_2$(dba)$_3$(Tris(dibenzylideneacetone)dipalladium(0)), Pd$_2$(dba)$_3$·CHCl$_3$, Pd(t-Bu$_3$P)$_2$ (Bis(tri-tert-butylphosphine)palladium(0)), Pd(acac)$_2$(Bis (acetylacetonato)palladium(II)), [Pd(allyl)Cl]$_2$ (Allylpalladium(II) chloride dimer), Pd(MeCN)$_2$Cl$_2$ (Dichlorobis(acetonitrile)palladium(II)), Pd(TFA)$_2$ (Palladium(II) Trifluoroacetate), Pd(OAc)$_2$(Palladium(II) Acetate), Pd(PCy$_3$)$_2$Cl$_2$(Dichlorobis(tricyclohexylphosphine)palladium(II)), Pd(PPh)$_2$Cl$_2$, Pd[P(o-tol)$_3$]$_2$Cl$_2$(Bis [tris(2-methylphenyl)phosphine]palladium), Pd(amphos)Cl$_2$ (Bis[di-tert-butyl(4-dimethylaminophenyl)phosphine] dichloropalladium(II)), Pd(dppf)Cl$_2$([1,1'-Bis (diphenylphosphino)ferrocene]dichloropalladium(II)), Pd(dppf)Cl$_2$·CH$_2$Cl$_2$, Pd(dtbpf)Cl$_2$([1,1'-Bis(di-tert-butylphosphino)ferrocene]dichloropalladium(II)), Pd(MeCN)$_4$(BF4)$_2$(Tetrakis(acetonitrile)palladium(II) tetrafluoroborate), PdBr$_2$, PdCl$_2$, cataCXium (registered trademark) C, Pd-PEPPSI-IPr, Pd-PEPPSI-SIPr, Pd-PEPPSI-IPent, and Pd/C. Preferable are Pd(PPh$_3$)$_4$, Pd(dba)$_2$, Pd$_2$(dba)$_3$, Pd$_2$(dba)$_3$·CHCl$_3$, Pd(amphos)Cl$_2$, Pd(dppf)Cl$_2$, Pd(dppf)Cl$_2$·CH$_2$Cl$_2$, Pd(dtbpf)Cl$_2$, and Pd-PEPPSI-IPr. More preferable are Pd$_2$(dba)$_3$·CHCl$_3$, Pd(amphos)Cl$_2$, Pd(dtbpf)Cl$_2$. The Pd catalysts may be used singly or in combination of two or more.

The amount of the metal catalyst used in the synthesis reaction of the vadadustat intermediate (3) is, for example, 0.0005 mol or more, preferably 0.005 mol or more, and more preferably 0.01 mol or more per mole of the compound (1). The upper limit thereof is, for example, 0.5 mol or less, preferably 0.3 mol or less, more preferably 0.1 mol or less, and further preferably 0.05 mol or less. Hereinafter, the substance amount of the metal catalyst per mole of the compound (1) may be referred to as "equivalent (eq)". As will be described later, the synthesis reaction of the vadadustat intermediate (3) may be performed in a batch reactor or in a flow reactor. The amount of the metal catalyst used is applicable both to the case of performing the synthesis reaction in a batch reactor and to the case of performing the synthesis reaction in a flow reactor. The amount of the metal catalyst used in the case of performing the synthesis reaction in a flow reactor is particularly preferably 0.05 mol or less per mole of the compound (1).

Ligand

In the synthesis reaction of the vadadustat intermediate (3), a ligand may be added together with the metal catalyst as necessary.

Examples of the ligand include monodentate phosphine ligands such as PMe$_3$(trimethylphosphine), P(t-Bu)$_3$(Tri-tert-butylphosphine), TTBP·HBF$_4$(Tri-tert-butylphosphine tetrafluoroborate), P(n-Oct)$_3$(Trioctylphosphine), P(Cy)$_3$ (Tricyclohexylphosphine), P(Cy)$_3$·HBF$_4$, P(o-tol)$_3$(Tris(2-methylphenyl)phosphine), Me$_2$PPh(Dimethylphenylphosphine), TFP(Tri(2-furyl)phosphine), Diphenyl-2-pyridylphosphine, Tris(hydroxymethyl)phosphine, KPPh$_2$, Ph$_2$PLi, P(i-Pr)$_2$Cl, P(t-Bu)$_2$Cl, Cy$_2$PCl, P(OMe)$_3$, P(OEt)$_3$, P(OPh)$_3$, 2-Chloro-4,4,5,5-tetramethyl-1,3,2-dioxaphospholane, TOPO(Tri-n-octylphosphine oxide), HPOPh$_2$, Ph$_2$POCl, TPPO(triphenylphosphine oxide), PhPOCl$_2$, Di-tert-butyl N,N-diisopropylphosphoramidite, Bis(diisopropylamino)chlorophosphine, HMPT(Tris(dimethylamino)phosphine), P(NEt$_2$)$_3$, Triphos(1,1,1-Tris (diphenylphosphinomethyl)ethane), PhPCl$_2$, Et$_2$PCl, BippyPhos(5-(Di-tert-butylphosphino)-1',3',5'-triphenyl-1'H-(1,4')bipyrazole), QPhos(1,2,3,4,5-Pentaphenyl-1'-(di-tert-butylphosphino)ferrocene), PTA(1,3,5-Triaza-7-phosphaadamantane), Bis(p-sulfonatophenyl)phenylphosphine dihydrate dipotassium salt, and amphos; bidentate phosphine ligands such as Xantphos(4,5-Bis(diphenylphosphino)-9,9-dimethylxanthene), DPEPhos(Bis[2-(diphenylphosphino)phenyl]ether), (6)-BINAP((f)-2,2'-Bis (diphenylphosphino)-1,1'-binaphthyl), dppbenz(1,2-Bis (diphenylphosphino)benzene), dppf(1,1'-Bis (diphenylphosphino)ferrocene), dmpe(1,2-Bis (dimethylphosphino)ethane), dppm(Bis (diphenylphosphino)methane), dppe(1,2-Bis (diphenylphosphino)ethane), dppp(1,3-Bis (diphenylphosphino)propane), dppb(1,4-Bis (diphenylphosphino)butane), 1,2-Bis(dichlorophosphino) ethane, dcpe(Bis(dicyclohexylphosphino)ethane), and dtbpf (Bis[(di-tert-butylphosphino)cyclopentadienyl]iron); Buchwald ligands such as Cyclohexyl JohnPhos((2-Biphenylyl)dicyclohexylphosphine), DavePhos(2-Dicyclohexylphosphino-2'-(N,N-dimethylamino)biphenyl), XPhos(2-Dicyclohexylphosphino-2',4',6'-triisopropylbiphenyl), SPhos(Dicyclohexyl[2',6'-dimethoxy-(1,1'-biphenyl)-2-yl] phosphine), MePhos(2-Dicyclohexylphosphino-2'-methylbiphenyl), RuPhos(2-Dicyclohexylphosphino-2',6'-diisopropoxybiphenyl), BrettPhos(2-Dicyclohexylphosphino-3, 6-dimethoxy-2',4',6'-triisopropyl-1,1'-biphenyl), sSPhos (Sodium 2'-dicyclohexylphosphino-2,6-dimethoxy-1,1'-biphenyl-3-sulfonate hydrate), PhDavePhos, tBuXPhos, JohnPhos(2-(Di-tert-butylphosphino)biphenyl), Tetramethyl di-tBuXPhos(2-Di-tert-butylphosphino-3,4,5,6-tetramethyl-2',4',6'-tri-1-propyl)-1,1'-biphenyl), tBuMePhos, tBuBrettPhos, tBuDavePhos, and JackiePhos(2-{Bis[3,5-Bis(trifluoromethyl)phenyl]phosphino}-3,6-dimethoxy-2',4',6'-triisopropyl-1,1'-biphenyl); cataCXium (registered trademark) ligands such as cataCXium A, cataCXium ABn, cataCXium AHI, cataCXium PtB, cataCXium PlntB, cataCXium PCy, and cataCXium POMetB; and DalPhos ligands such as Me-DalPhos and Mor-DalPhos. Preferable are amphos, dppf, dppb, dtbpf, tBuXPhos, cataCXium A, and the like. More preferable are a ligand (A), such as amphos and dtbpf, in which two alkyl groups having 4 to 8 carbon atoms and having a tertiary carbon atom and one monocyclic aromatic ring that may be substituted with an amino group or a hydrocarbon group having 1 to 20 carbon atoms are bonded to a phosphorus atom, and a ligand (B) in which two of the ligands (A) are ferrocenylated with Fe. The ligands may be used singly or in combination of two or more.

The amount of the ligand used in the synthesis reaction of the vadadustat intermediate (3) is, for example, 0.002 mol or more, preferably 0.02 mol or more, and more preferably 0.04 mol or more per mole of the compound (1). The upper limit thereof is, for example, 2.0 mol or less, preferably 1.2 mol or less, more preferably 0.4 mol or less. Hereinafter, the substance amount of the ligand per mole of the compound (1) may be referred to as "equivalent (eq)".

Solvent

In the synthesis reaction of the vadadustat intermediate (3), a reaction solvent may also be used as necessary.

The solvent is not particularly limited so long as it does not affect the reaction. Specifically, for example, ether-based solvents such as tetrahydrofuran, methyl tetrahydrofuran, diethyl ether, 1,4-dioxane, methyl tert-butyl ether, and 1,2-dimethoxyethane; nitrile-based solvents such as acetonitrile, propionitrile, and isobutyronitrile; ester-based solvents such as ethyl acetate, n-propyl acetate, and isopropyl acetate; aliphatic hydrocarbon-based solvents such as pentane, hexane, heptane, and methylcyclohexane; aromatic hydrocarbon-based solvents such as benzene, toluene, xylene, ethylbenzene, and mesitylene; ketone-based solvents such as acetone, methyl ethyl ketone, and methyl isobutyl ketone; halogen-based solvents such as methylene chloride and 1,2-dichloroethane; sulfoxide-based solvents such as dimethyl sulfoxide; amide-based solvents such as N,N-dimethylformamide, N,N-dimethylacetamide, N,N-diethylacetamide, N-methyl-2-pyrrolidone, N-ethyl-2-pyrrolidone, N-methyl-ε-caprolactam, and hexamethylphosphoramide; urea-based solvents such as dimethylpropylene urea; phosphonic acid triamide-based solvents such as hexamethylphosphonic acid triamide; and the like can be used. The solvents may be used singly or in combination of two or more. When two or more solvents are used in combination, there is no restriction on the mixing ratio thereof.

In the present invention, from the viewpoint of improving reactivity, ether-based solvents, ester-based solvents, aromatic hydrocarbon-based solvents, ketone-based solvents, and amide-based solvents are preferable; 1,2-dimethoxyethane, isopropyl acetate, toluene, acetone, methyl isobutyl ketone, N,N-dimethylformamide, and N,N-dimethylacetamide are more preferable; and methyl isobutyl ketone, N,N-dimethylformamide, and N,N-dimethylacetamide are further preferable.

The amount of the solvent used in the synthesis reaction of the vadadustat intermediate (3) is, for example, 0.5 parts by mass or more, preferably 1 part by mass or more, and more preferably 2 parts by mass or more, and is, for example, 80 parts by mass or less, preferably 60 parts by mass or less, and more preferably 40 parts by mass or less with respect to 1 part by mass of the compound (1).

Base

In the synthesis reaction of the vadadustat intermediate (3), a base may be added in order to further accelerate the reaction.

The base is preferably a nitrogen-containing organic compound. Examples of the nitrogen-containing organic compound include tertiary amines such as trimethylamine, triethylamine, tripropylamine, tributylamine, tripentylamine, trihexylamine, triheptylamine, trioctylamine, tridodecylamine, dodecyldimethylamine, hexyldibutylamine, diisopropylbutylamine, diisopropylethylamine, dimethylethylamine, dicyclohexylmethylamine, N-methylpyrrolidine, quinuclidine, N-methylmorpholine, 1,4-diazabicyclo[2,2,2]octane, 1,8-diazabicyclo[5,4,0]-7-undecene, pyridine, 2-picoline, 3-picoline, 2,6-lutidine, collidine, 4-dimethylaminopyridine, quinoline, and N-methylimidazole. The bases may be used singly or in combination of two or more. When two or more bases are used in combination, there is no restriction on the mixing ratio thereof.

The base is more preferably a non-aromatic tertiary amine such as tributylamine, diisopropylethylamine, 1,8-diazabicyclo[5,4,0]-7-undecene, and N-methylmorpholine, and further preferably a trialkylamine such as tributylamine and diisopropylethylamine (particularly, an amine having three alkyl groups each having 1 to 8 carbon atoms).

The amount of the base used in the synthesis reaction of the vadadustat intermediate (3) is, for example, preferably 0.5 mol or more, more preferably 1.0 mol or more, further preferably 1.3 mol or more, and still further preferably 1.5 mol or more per mole of the compound (1). The upper limit thereof is not particularly limited, and is preferably 5.0 mol or less, more preferably 4.5 mol or less, and further preferably 4.0 mol or less. Hereinafter, the substance amount of the base per mole of the compound (1) may be referred to as "equivalent (eq)".

Production of Vadadustat Intermediate (3)

A reaction for synthesizing the vadadustat intermediate (3) is performed by reacting the compound (1) with the compound (2) in the presence of carbon monoxide and, as necessary, the metal catalyst, the ligand, the solvent, and the base. The reaction may be performed in a batch reactor or in a flow reactor.

The flow reactor means a micro flow reactor including a mixing unit to contact a plurality of liquids or gases with each other and mix them, and a reactor unit (retention line) connected downstream of the mixing unit. A liquid containing a reagent is fed to the mixing unit using a liquid feed device such as a pump, and a gas is fed to the mixing unit using a flow control device such as a mass flow controller, and the resulting mixture passes through the reactor unit and is continuously discharged from a discharge unit as a product.

The FIGURE is a schematic view showing an example of the configuration of a flow reactor that can be used in the present invention. As shown in this example, the flow reactor used for the synthesis reaction of the vadadustat intermediate (3) includes two or more raw material feeding units (a carbon monoxide feeding unit 1a and a raw material solution feeding unit 1b for the compound (1), the compound (2) and the like in the example of the FIGURE), a first mixing unit (a mixing unit 2 in the example of the FIGURE) to mix raw materials fed from these raw material feeding units, and a reactor unit (a tubular reactor unit 3 in the example of the FIGURE) through which a mixture prepared in the first mixing unit flows. The reaction proceeds while the mixture flows through the reactor unit. The boundary between the mixing unit and the reactor unit does not have to be clear, and may change seamlessly. The flow channels of the mixing unit and the reactor unit may be a fine flow channel, a linear flow channel such as a tube, a planar flow channel such as a disk that rotates about a rotation axis (also called a rotating disk), or a continuous vessel flow channel. As a specific example of a flow reactor with the flow channels of the mixing unit and the reactor unit being a planar flow channel, SpinPro R10 or R300 manufactured by Flowid can be mentioned. As a specific example of a flow reactor with the flow channels of the mixing unit and the reactor unit being a continuous vessel flow channel, an agitated cell reactor (ACR), an agitated tube reactor (ATR), or a rotating tube reactor (RTR) manufactured by AM Technology can be mentioned. Further, when necessary, a second mixing unit may be provided on the upstream side of the raw material solution feeding unit 1b, the compound (1) and the compound (2) separately fed may be mixed in the second mixing unit and then fed to the first mixing unit.

The flow reactor may include a temperature control device (a temperature control room, a temperature control bath, a jacket container, a heat medium flow channel, or the like; in the example of the FIGURE, a temperature control bath; temperature control device 7) that is capable of adjusting the temperature of at least one of the raw material feeding unit, the mixing unit, and the reactor unit.

(a) Flow Reactor Having Linear Flow Channel Reactor Unit

The raw material feeding unit of the flow reactor having a linear flow channel reactor unit is preferably tubular, and the inner diameter of the tube is preferably 0.01 mm or more, more preferably 0.1 mm or more, and further preferably 0.3 mm or more, and is preferably 50 mm or less, more preferably 20 mm or less, and further preferably 10 mm or less.

The mixing unit of the flow reactor having the linear flow channel reactor unit is preferably tubular, and the inner diameter of the tube is preferably 0.01 mm or more and 50 mm or less.

The mixing unit of the flow reactor having the linear flow channel reactor unit may be provided with a known mixer in order to sufficiently stir raw materials fed from the raw material feeding unit. Examples of such a mixer include a T-shape mixer, a Y-shape mixer, a V-shape mixer, a static mixer, a helix-type mixer, and the like. In the example of the FIGURE, a T-shape mixer is used.

In the flow reactor having the linear flow channel reactor unit, the cross section of the flow channel of the reactor unit may be circular, polygonal, or distorted circular (for example, convex or concave), and the circular or polygonal cross section is preferable. Further, the reactor unit may have a straight tube structure or a structure with many bent backs, and may take various shapes. In the example of the FIGURE, a tubular reactor having a helical structure is used.

In the flow reactor having the linear flow channel reactor unit, the length of the reactor unit may be appropriately set according to the reaction time (retention time), and is, for example, 1 cm or more, preferably 10 cm or more, more preferably 50 cm or more, particularly preferably 1 m or more, and most preferably 3 m or more. The upper limit of the length of the reactor unit is not particularly limited, and is, for example, 500 m or less, preferably 300 m or less, more preferably 200 m or less, further preferably 100 m or less, and particularly preferably 50 m or less.

In the flow reactor having the linear flow channel reactor unit, the equivalent diameter of the flow channel of the reactor unit is preferably 50 mm or less, more preferably 20 mm or less, and further preferably 15 mm or less. In view of pressure drop, the equivalent diameter of the flow channel of the reactor unit is preferably 0.05 mm or more, more preferably 0.1 mm or more, and further preferably 0.3 mm or more.

In the present invention, the "equivalent diameter of the flow channel" indicates a diameter of a circular tube regarded as equivalent to the cross section of the flow channel. That is, the equivalent diameter De of the flow channel is represented by the following formula (i):

$$De = 4Af/Wp \qquad (i)$$

wherein Af is a cross sectional area of a flow channel, and Wp is a wet perimeter (the length of the wall in the cross section).

When the linear flow channel reactor unit has a helical shape, an apparent volume (S×H) of a helix determined from a length (H) of a traveling axis of the helix and an area (S) of a helix projected on a plane orthogonal to the traveling axis (hereinafter may be referred to simply as "projected area") is, for example, 0.5% or more, preferably 2% or more, and more preferably 10% or more, and for example, 90% or less, preferably 80% or less, and more preferably 60% or less with respect to a size (internal capacity, etc.) of the temperature control device (a temperature control room, a temperature control bath, a jacket container, a heat medium flow channel, or the like; in the example of the FIGURE, the temperature control bath; temperature control device 7).

(b) Flow Reactor Having Planar Flow Channel Reactor Unit

The raw material feeding unit of the flow reactor having a planar flow channel reactor unit (hereinafter also referred to as a planar reactor unit) is preferably tubular, and the inner diameter of the tube is preferably 0.01 mm or more, and more preferably 0.1 mm or more, and is preferably 50 mm or less.

The mixing unit of the flow reactor having the planar reactor unit is preferably planar. The flow channel width of the mixing unit is preferably 0.01 mm or more and 50 mm or less. The mixing unit of the flow reactor having the planar reactor unit indicates a part which is located between the end of the raw material feeding unit and the inlet of the reactor unit and where raw materials are mixed, and the upstream part of the planar flow channel also serves as the mixing unit.

In the mixing unit of the flow reactor having the planar reactor unit, a raw material mixture is sufficiently stirred by high-speed rotation of the rotating disk and fed to the reactor unit as a reaction solution. The reactor unit of the flow reactor having the planar reactor unit also serves as a downstream part of the planar flow channel.

The equivalent length of the planar reactor unit may be appropriately set according to the reaction time (retention time), and is, for example, 1 cm or more, and preferably 10 cm or more. The upper limit of the length of the reactor unit is not particularly limited, and is, for example, 500 m or less, preferably 300 m or less, and more preferably 100 m or less. In the present invention, the "equivalent length of the planar reactor unit" indicates a length equivalent to a distance over which the reaction solution flows in the flow channel in the reactor unit.

The width of the reaction flow channel of the planar reactor unit is preferably 0.01 mm or more and 50 mm or less.

The number of rotating disks in the flow reactor having the planar reactor unit is, for example, 100 or less, preferably 50 or less, and more preferably 10 or less and is, for example, 1 or more, and preferably 3 or more.

The thickness of the rotating disk is, for example, 0.01 cm or more, preferably 0.05 cm or more, and more preferably 0.1 cm or more, and is, for example, 10 cm or less, preferably 5 cm or less, and more preferably 1 cm or less.

The rotation speed of the rotating disk may be appropriately set according to the compound (1), the compound (2), the types of metal catalyst, ligand, solvent, and base to be used as necessary, and the reaction temperature. The rotation speed of the rotating disk is, for example, 250 rpm or more, preferably 500 rpm or more, and more preferably 1000 rpm or more, and is, for example, 32000 rpm or less, preferably 16000 rpm or less, and more preferably 8000 rpm or less.

When the reaction for synthesizing the vadadustat intermediate (3) is performed in a batch reactor, a gaseous phase portion in a reaction vessel may be replaced with carbon monoxide (or a mixed gas thereof), or carbon monoxide (or a mixed gas thereof) may be bubbled into a liquid phase portion in the reaction vessel. When carbon monoxide is introduced in the batch reactor, the gaseous phase portion may be pressurized (gauge pressure: more than 0 MPa) or may be at normal pressure (gauge pressure: 0 MPa). When the gaseous phase portion is pressurized, the gauge pressure in the gaseous phase portion can be, for example, 0.1 MPa or more, preferably 0.2 MPa or more, and more preferably 0.3 MPa or more. The upper limit of the gauge pressure can be appropriately set according to the pressure resistance of an apparatus, and is, for example, 3 MPa or less, preferably 2 MPa or less, and more preferably 1 MPa or less.

When the reaction for synthesizing the vadadustat intermediate (3) is performed in a flow reactor, carbon monoxide or a mixed gas thereof (preferably a single gas of carbon monoxide) may be fed while controlling the flow rate using a mass flow controller or the like. The reaction for synthesizing the vadadustat intermediate (3) performed in the flow reactor does not require an excessive amount of carbon monoxide as in the reaction performed in the batch reactor, and the reaction can be favorably performed with only about the chemically equivalent amount of carbon monoxide.

The amount of carbon monoxide used when the vadadustat intermediate (3) is synthesized in the flow reactor is, for example, preferably 0.5 mol or more, more preferably 0.8 mol or more, and further preferably 1.0 mol or more, and is, for example, preferably 4.0 mol or less, more preferably 3.5 mol or less, and further preferably 3.0 mol or less, per mole of the compound (1). Hereinafter, the substance amount of carbon monoxide per mole of the compound (1) may be referred to as "equivalent (eq)".

When the synthesis reaction of the vadadustat intermediate (3) is performed in the batch reactor, the reaction temperature is not particularly limited, and is, for example, 0° C. or higher, preferably 10° C. or higher, and more preferably 20° C. or higher is, for example, 400° C. or lower, preferably 300° C. or lower, and more preferably 200° C. or lower.

When the synthesis reaction of the vadadustat intermediate (3) is performed in the batch reactor, the reaction time may be appropriately set according to the compound (1), the compound (2), the types of metal catalyst, ligand, solvent, and base to be used as necessary, and the reaction temperature. The reaction time is, for example, 0.5 hours or more, preferably 1 hour or more, and more preferably 1.5 hours or more, and is, for example, 48 hours or less, preferably 24 hours or less, and more preferably 12 hours or less.

When the synthesis reaction of the vadadustat intermediate (3) is performed in the flow reactor, the reaction temperature is not particularly limited, and is, for example, 0° C. or higher, preferably 30° C. or higher, and more preferably 60° C. or higher, and high-temperature conditions of 80° C. or higher are further preferable. The reaction temperature is, for example, 400° C. or lower, preferably 300° C. or lower, and more preferably 200° C. or lower. When the synthesis reaction of the vadadustat intermediate (3) is performed in the flow reactor, the reaction conversion rate tends to be higher when the reaction is performed under high-temperature conditions.

When the synthesis reaction of the vadadustat intermediate (3) is performed in the flow reactor, the reaction time may be appropriately set according to the compound (1), the compound (2), the types of metal catalyst, ligand, solvent, and base to be used as necessary, and the reaction temperature. The reaction time is, for example, 1 minute or more, preferably 10 minutes or more, and more preferably 30 minutes or more, and is, for example, 8 hours or less, preferably 4 hours or less, and more preferably 2 hours or less.

When the synthesis reaction of the vadadustat intermediate (3) is performed in the flow reactor, the reaction is preferably performed under a pressurized condition. By performing the reaction under a pressurized condition, the reaction conversion rate can be further increased. The reaction pressure (gauge pressure) is, for example, preferably 0.05 MPa or more, more preferably 0.1 MPa or more, and further preferably 0.3 MPa or more, and is, for example, preferably 20 MPa or less, more preferably 10 MPa or less, and further preferably 1 MPa or less. The pressure control in the reaction system can be performed by a back pressure valve or the like (a back pressure valve 6 in the example of the FIGURE) connected downstream of the reactor unit.

When the synthesis reaction of the vadadustat intermediate (3) is performed in the flow reactor, the pressure (gauge pressure) of carbon monoxide (or a mixed gas thereof) to be fed is, for example, preferably 0.05 MPa or more, more preferably 0.1 MPa or more, and further preferably 0.3 MPa or more, and is, for example, preferably 40 MPa or less, more preferably 20 MPa or less, and further preferably 10 MPa or less.

When the synthesis reaction of the vadadustat intermediate (3) is performed in the flow reactor, a gas-liquid mixed flow formed in the reactor is, for example, a bubble flow, a slug flow, a froth flow, an annular mist flow (annular spray flow), an annular flow (circular flow), a mist flow (spray flow), or the like, and is preferably a slug flow.

When the synthesis reaction of the vadadustat intermediate (3) is performed in the flow reactor, the flow rate at which carbon monoxide, the compound (1), and the compound (2) flow through the raw material feeding unit, and the flow rate at which a raw material mixture flows through the reactor unit may be appropriately set according to the compound (1), the compound (2), the types of metal catalyst, ligand, solvent, and base to be used as necessary, the reaction temperature, and the retention time in the reactor unit.

It is preferred to perform the synthesis reaction of the vadadustat intermediate (3) in the flow reactor rather than in the batch reactor from the viewpoint of safety and reduction of reaction time.

Vadadustat Intermediate (3)

The first vadadustat intermediate represented by the following formula (3) can be produced by reaction of the compound (1) with the compound (2) in the presence of carbon monoxide:

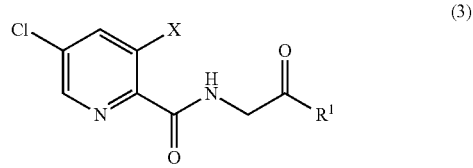

wherein R¹ and X are the same as the above.

Specific examples and preferred ranges of R¹ and X in the vadadustat intermediate (3) are the same as the above.

The obtained vadadustat intermediate (3) may be subjected to isolation or purification as needed, and to that end, conventional separation methods such as extraction, concentration, crystallization, column chromatography and the like may be appropriately combined. However, from the viewpoint of simplifying the production process, it is preferred to, without subjecting the vadadustat intermediate (3) to aftertreatment such as isolation or purification, use the reaction solution containing the vadadustat intermediate (3) as it is in the reaction of the next step.

Production of Vadadustat Intermediate (4)

The reaction solution containing the vadadustat intermediate (3) is subjected to isolation or purification as needed (preferably without being subjected to aftertreatment), and subsequently reacted with 3-chlorophenylboronic acid, whereby the following vadadustat intermediate (4) can be synthesized. The reaction may be performed in a batch reactor or in a flow reactor. When the reaction solution containing the vadadustat intermediate (3) is used without aftertreatment, the reaction solution containing the vadadustat intermediate (3) may be added to a reaction vessel (such as a vessel 8 in the example of the FIGURE) into which 3-chlorophenylboronic acid has been placed, or 3-chlorophenylboronic acid may be added to a reaction vessel into which the reaction solution containing the vadadustat intermediate (3) has been placed:

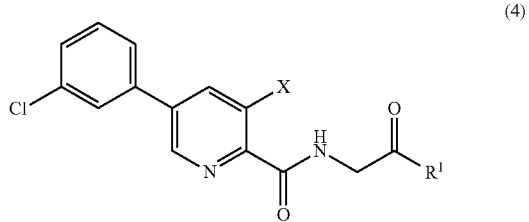

(4)

wherein $R^1$ and X are the same as the above.

The amount of 3-chlorophenylboronic acid used in the synthesis of the vadadustat intermediate (4) is, for example, preferably 0.5 mol or more, and more preferably 0.8 mol or more, and is, for example, preferably 5.0 mol or less, and more preferably 3.0 mol or less per mole of the compound (1) in the synthesis of the vadadustat intermediate (3). Hereinafter, the substance amount of 3-chlorophenylboronic acid per mole of the compound (1) may be referred to as "equivalent (eq)".

In the synthesis reaction of the vadadustat intermediate (4), one or more selected from the group consisting of a metal catalyst, a ligand, a solvent, a base, and a phase transfer catalyst may also be used.

As a metal catalyst, a ligand, and a solvent used in the synthesis reaction of the vadadustat intermediate (4), the same metal catalysts, ligands, and solvents as those that may be used in the synthesis reaction of the vadadustat intermediate (3) can be mentioned, and the preferred ranges thereof are also the same.

As a metal catalyst used in the synthesis reaction of the vadadustat intermediate (4), the same metal catalyst as that used in the synthesis reaction of the vadadustat intermediate (3) is preferably used. The use of the same catalyst allows the production process to be simplified and the kinds of impurities generated in the reaction to be reduced.

As a metal catalyst used in the synthesis reaction of the vadadustat intermediate (4), when the vadadustat intermediate (3) is not subjected to aftertreatment, the metal catalyst used in the synthesis reaction of the vadadustat intermediate (3) may be continuously used, or a metal catalyst may be further added as needed during the synthesis reaction of the vadadustat intermediate (4). From the viewpoint of simplifying the production process, the metal catalyst used in the synthesis reaction of the vadadustat intermediate (3) may be continuously used as a metal catalyst to be used for the synthesis reaction of the vadadustat intermediate (4), and a metal catalyst need not be added during the synthesis reaction of the vadadustat intermediate (4). On the other hand, when a metal catalyst is further added during the synthesis reaction of the vadadustat intermediate (4), the amount of addition of the metal catalyst (equivalents (eq) with respect to the compound (1)) is, for example, 0.0005 mol or more, preferably 0.005 mol or more, and more preferably 0.01 mol or more per mole of the compound (1) in the synthesis of the vadadustat intermediate (3). The upper limit of the amount of addition of the metal catalyst is, for example, 0.3 mol or less, preferably 0.2 mol or less, and more preferably 0.1 mol or less.

As a ligand used in the synthesis reaction of the vadadustat intermediate (4), the same ligand as that used in the synthesis reaction of the vadadustat intermediate (3) is preferably used.

As a ligand used in the synthesis reaction of the vadadustat intermediate (4), when the vadadustat intermediate (3) is not subjected to aftertreatment, the ligand used in the synthesis reaction of the vadadustat intermediate (3) may be continuously used, or a ligand may be further added as needed during the synthesis reaction of the vadadustat intermediate (4). From the viewpoint of simplifying the production process, the ligand used in the synthesis reaction of the vadadustat intermediate (3) may be continuously used as a ligand to be used for the synthesis reaction of the vadadustat intermediate (4), and a ligand need not be added during the synthesis reaction of the vadadustat intermediate (4). On the other hand, when a ligand is further added during the synthesis reaction of the vadadustat intermediate (4), the amount of addition of the ligand (equivalents (eq) with respect to the compound (1)) is, for example, 0.002 mol or more, preferably 0.02 mol or more, and more preferably 0.04 mol or more per mole of the compound (1) in the synthesis of the vadadustat intermediate (3). The upper limit of the amount of addition of the ligand is, for example, 1.2 mol or less, preferably 0.8 mol or less, and more preferably 0.4 mol or less.

A solvent used in the synthesis reaction of the vadadustat intermediate (4) can be selected from the same range as that of the solvents exemplified in the synthesis reaction of the vadadustat intermediate (3) and is preferably the same solvent as that used in the synthesis reaction of the vadadustat intermediate (3). The use of the same solvent allows easy reuse of the solvent. When the vadadustat intermediate (3) is not subjected to aftertreatment, the solvent used in the synthesis reaction of the vadadustat intermediate (3) may be continuously used as a solvent to be used for the synthesis reaction of vadadustat intermediate (4), and a solvent may be further added as needed during the synthesis reaction of the vadadustat intermediate (4). By not further adding a solvent during the synthesis reaction of the vadadustat intermediate (4) and continuing to use the solvent used in the synthesis reaction of the vadadustat intermediate (3), the production process can be simplified.

A base used in the synthesis reaction of the vadadustat intermediate (4) may be an inorganic base or an organic base. Examples of the inorganic base include metal hydroxides such as sodium hydroxide, potassium hydroxide, barium hydroxide, and thallium hydroxide; alkali metal carbonates such as sodium carbonate, potassium carbonate, and cesium carbonate; alkali metal hydrogen carbonates such as sodium hydrogen carbonate and potassium hydrogen carbonate; alkali fluoride metal salts such as potassium fluoride and cesium fluoride; alkali metal phosphates such as sodium phosphate and potassium phosphate; and alkali metal alkoxides such as sodium methoxide, sodium ethoxide, potassium methoxide, and potassium ethoxide. From the viewpoint of basic strength, alkali metal carbonates such as sodium carbonate and potassium carbonate are preferable. As the organic base, a nitrogen-containing organic compound is preferable, and examples thereof include primary amines such as methylamine and ethylamine; secondary amines such as dimethylamine, diethylamine, and diisopropylamine; and tertiary amines such as trimethylamine, triethylamine, and diisopropylethylamine, and tertiary amines are preferable.

The amount of the base used in the synthesis reaction of the vadadustat intermediate (4) is, for example, preferably 0.5 mol or more, more preferably 0.8 mol or more, and further preferably 1.0 mol or more, and is, for example, preferably 5.0 mol or less, more preferably 4.0 mol or less, and further preferably 3.0 mol or less, per mole of the compound (1) in the synthesis reaction of the vadadustat intermediate (3). Hereinafter, the substance amount of the base per mole of the compound (1) may be referred to as "equivalent (eq)". Examples of the phase transfer catalyst used in the synthesis reaction of the vadadustat intermediate (4) include quaternary ammonium salts such as tetrabutylammonium chloride, benzyltributylammonium chloride, tetrabutylammonium fluoride, and tetrabutylammonium bromide; phosphonium salts such as tributyl(cyanomethyl) phosphonium chloride and tributyldodecylphosphonium bromide; and crown ethers such as 12-crown-4 and 15-crown-5. Quaternary ammonium salts are preferable, and tetrabutylammonium chloride, tetrabutylammonium fluoride, and tetrabutylammonium bromide are more preferable.

The amount of the phase transfer catalyst used in the synthesis reaction of the vadadustat intermediate (4) is, for example, preferably 0.01 mol or more, more preferably 0.1 mol or more, and is, for example, preferably 5 mol or less, more preferably 1 mol or less, per mole of the compound (1) in the synthesis reaction of the vadadustat intermediate (3). Hereinafter, the substance amount of the phase transfer catalyst per mole of the compound (1) may be referred to as "equivalent (eq)".

Production of Vadadustat

As a method for producing vadadustat from the vadadustat intermediate (4), the method disclosed in Chinese Patent Application Publication No. 105837502 may be used as it is or with appropriate modification. For example, the outline can be expressed by the following formula. When the vadadustat intermediate (4) is a compound of the formula (4a) in which X is a chlorine atom, the compound is treated with an alkoxide of an alkali metal (M) (which is represented by $R^{10}OM$ in the following formula; for example, sodium methoxide) and further treated with an acid (for example, hydrogen bromide), whereby vadadustat can be produced. When the vadadustat intermediate (4) is a compound of the formula (4b) in which X is a hydroxy group or $OP^1$ (except when becoming a compound of the formula (4c)), the compound is treated with an acid (for example, hydrogen bromide), whereby vadadustat can be produced. When the vadadustat intermediate (4) is a compound of the formula (4c) in which X is a hydroxy group and $R^1$ is a hydroxy group, this intermediate (4c) is vadadustat.

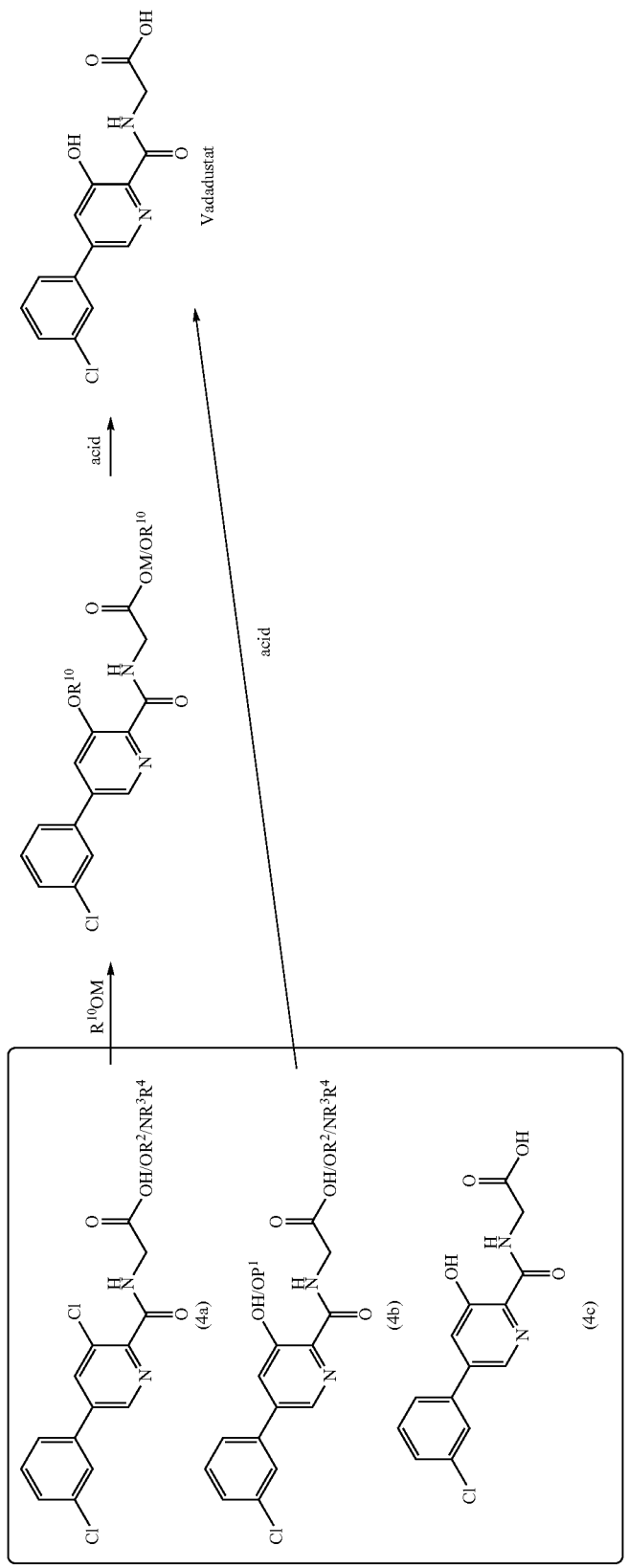

The present application claims priority based on Japanese Patent Application No. 2019-086759 filed on Apr. 26, 2019. All the contents described in Japanese Patent Application No. 2019-086759 filed on Apr. 26, 2019 are incorporated herein by reference.

EXAMPLES

The present invention will be more specifically explained below with reference to specific examples; however, the present invention is not restricted by the below examples and can be put into practice after appropriate modifications within a range meeting the gist of the above and the below, all of which are included in the technical scope of the present invention.

The conversion rate and the yield of each compound described in Examples 1 to 24 below were calculated based on the analysis results by high performance liquid chromatography (HPLC) method. The HPLC conditions were as follows.

Column: COSMOSIL 5C18-AR-II (4.6 mm I.D.×250 mm) (manufactured by Nacalai Tesque, Inc.)
Mobile phase A: 0.1% phosphoric acid aqueous solution
Mobile phase B: Acetonitrile
Flow rate: 1.0 mL/min
Detection wavelength: UV 220 nm
Column temperature: 30° C.
Gradient condition:

| Time (minutes) | Liquid A (%) | Liquid B (%) |
| --- | --- | --- |
| 0 | 95 | 5 |
| 25.0 | 5 | 95 |
| 28.0 | 5 | 95 |
| 28.1 | 95 | 5 |
| 35.0 | 95 | 5 |

Retention time: 2-Bromo-3,5-dichloropyridine: 24.5 minutes, N-(3,5-dichloropyridin-2-carbonyl)glycine methyl ester: 16.7 minutes, N-(3,5-dichloropyridin-2-carbonyl)glycine tert-butyl ester: 18.4 minutes, N-[5-(3-chlorophenyl)-3-chloropyridin-2-carbonyl]glycine methyl ester: 21.9 minutes, and N-[5-(3-chlorophenyl)-3-chloropyridin-2-carbonyl]glycine: 19.4 minutes In addition, if necessary, the outlet of the reaction tube was connected to React IR15 (manufactured by METTLER TOLEDO Co., Ltd.), and the reaction conversion rate was confirmed in real time.

Characteristic peak: 2-Bromo-3,5-dichloropyridine: 833 $cm^{-1}$, and N-(3,5-dichloropyridin-2-carbonyl)glycine methyl ester: 862 $cm^{-1}$ Example 1

Production of Vadadustat Intermediate (3x) (Batch Reaction)

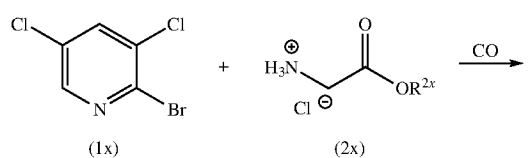

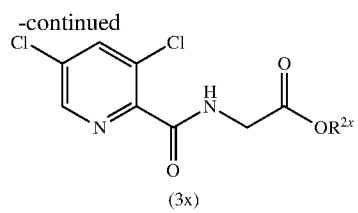

Into a reaction vessel were placed 0.50 g (2.2 mmol) of 2-Bromo-3,5-dichloropyridine (1x), 0.42 g (3.3 mmol, 1.5 eq) of glycine ester hydrochloride (2x) ($R^{2x}$=methyl group (Me)), 2.50 g (5 times the mass of (1x)) of dimethylacetamide, and 0.87 g (5.7 mmol, 2.6 eq) of 1,8-diazabicyclo[5.4.0]-7-undecene in this order, and then, degassing under reduced pressure and replacement by nitrogen were performed three times. Next, 0.11 g (0.11 mmol, 0.05 eq) of $Pd_2(dba)_3 \cdot CHCl_3$ and 0.21 g (0.44 mmol, 0.20 eq) of dtbpf were added thereto, and then, degassing under reduced pressure and replacement by nitrogen were performed three times. Subsequently, degassing under reduced pressure and replacement by carbon monoxide were performed three times, and then the mixture was reacted at 80° C. under normal pressure (0 MPaG) for 5 hours to produce a vadadustat intermediate (3x). The obtained reaction solution was analyzed, and the conversion rate was found to be 99.4%.

Conversion rate = Production amount (mol) of compound (3x)/(Production amount (mol) of compound (3x) + Remaining amount (mol) of compound (1x))×100(%)

Examples 2 to 18

Production of Vadadustat Intermediate (3x) (Batch Reaction)

A vadadustat intermediate (3x) was produced in the same manner as in Example 1 except that the type ($R^{2x}$) and the equivalent of the glycine ester hydrochloride (2x), the type and the use amount of the solvent, the type and the equivalent of the base, the type and the equivalent of the metal catalyst, the type of the ligand, the reaction temperature, and the reaction time were changed as shown in Tables 1 and 2.

Example 19

Production of Vadadustat Intermediate (3x) (Flow Reaction)

Into a raw material solution storage container were placed 0.50 g (2.2 mmol) of 2-Bromo-3,5-dichloropyridine (1x), 0.42 g (3.3 mmol, 1.5 eq) of glycine ester hydrochloride (2x) ($R^{2x}$=methyl group (Me)), 16.7 g (33 times the mass of (1x)) of dimethylacetamide, and 1.06 g (5.7 mmol, 2.6 eq) of tributylamine in this order, and then, degassing under reduced pressure and replacement by nitrogen were performed three times. Next, 0.11 g (0.11 mmol, 0.05 eq) of $Pd_2(dba)_3 \cdot CHCl_3$ and 0.21 g (0.44 mmol, 0.20 eq) of dtbpf were added thereto, and then, degassing under reduced pressure and replacement by nitrogen were performed three times to prepare a raw material solution.

The raw material solution prepared above was fed at a rate of 0.4 mL/min using a plunger pump (manufactured by FLOM Corporation), carbon monoxide was fed at a rate of 2.0 mL/min (2.0 eq) using a mass flow controller (manufactured by Nakamura Choukou Co., Ltd.), and the raw material solution and the carbon monoxide were mixed in a T-shape mixer (manufactured by EYELA, inner diameter: 2 mm) to thereby form a slug flow. Subsequently, the mixture was retained in a line (stainless steel, inner diameter: 2.17 mm, length: 9 m) for 0.8 hours to produce a vadadustat intermediate (3x), and then, the whole amount of the reaction solution was recovered from an outlet line. Incidentally, the retention line was heated to 120° C. using a temperature control device (manufactured by ThalesNano Inc.), and the reaction pressure (gauge pressure) was adjusted to 0.6 MPa using a back pressure valve (manufactured by Equilibar). The obtained reaction solution was analyzed, and the conversion rate was found to be 99% and the yield was found to be 84%.

Conversion rate = Production amount (mol) of compound (3x)/(Production amount (mol) of compound (3x) + Remaining amount (mol) of compound (1x)) × 100(%)

Examples 20 to 23

Production of Vadadustat Intermediate (3x) (Flow Reaction)

A vadadustat intermediate (3x) was produced in the same manner as in Example 19 except that the equivalent of the metal catalyst, the equivalent of the ligand, the feeding rate of the raw material solution, the feeding rate of the carbon monoxide, the inner diameter of the T-shape mixer, the reaction temperature, and the reaction pressure were changed as shown in Tables 1 and 2. In Example 23, a T-shape mixer manufactured by Swagelok was used.

TABLE 1

| | Reaction method | Glycine ester hydrochloride (2×) | | Solvent | | Base | | Metal catalyst | | Ligand | | CO |
|---|---|---|---|---|---|---|---|---|---|---|---|---|
| | | $R^{2x}$ | Equivalent | Type | Mass ratio | Type | Equivalent | Type | Equivalent | Type | Equivalent | Equivalent |
| Example 1 | batch | Me | 1.5 eq | DMA | 5 times | DBU | 2.6 eq | $Pd_2(dba)_3$•$CHCl_3$ | 0.05 eq | dtbpf | 0.20 eq | (excess) |
| Example 2 | batch | tert-Bu | 1.5 eq | DMA | 5 times | DBU | 2.6 eq | $Pd_2(dba)_3$•$CHCl_3$ | 0.05 eq | dtbpf | 0.20 eq | (excess) |
| Example 3 | batch | Me | 1.5 eq | DMA | 5 times | DIPEA | 2.6 eq | $Pd_2(dba)_3$•$CHCl_3$ | 0.05 eq | dtbpf | 0.20 eq | (excess) |
| Example 4 | batch | Me | 1.5 eq | DMA | 5 times | NMI | 2.6 eq | $Pd_2(dba)_3$•$CHCl_3$ | 0.05 eq | dtbpf | 0.20 eq | (excess) |
| Example 5 | batch | Me | 1.5 eq | DMA | 5 times | TBA | 2.6 eq | $Pd_2(dba)_3$•$CHCl_3$ | 0.05 eq | dtbpf | 0.20 eq | (excess) |
| Example 6 | batch | Me | 1.5 eq | DMA | 5 times | NMM | 2.6 eq | $Pd_2(dba)_3$•$CHCl_3$ | 0.05 eq | dtbpf | 0.20 eq | (excess) |
| Example 7 | batch | Me | 1.5 eq | DME | 5 times | TBA | 2.6 eq | $Pd_2(dba)_3$•$CHCl_3$ | 0.05 eq | dtbpf | 0.20 eq | (excess) |
| Example 8 | batch | Me | 1.5 eq | AcOiPr | 5 times | TBA | 2.6 eq | $Pd_2(dba)_3$•$CHCl_3$ | 0.05 eq | dtbpf | 0.20 eq | (excess) |
| Example 9 | batch | Me | 1.5 eq | DMF | 5 times | TBA | 2.6 eq | $Pd_2(dba)_3$•$CHCl_3$ | 0.05 eq | dtbpf | 0.20 eq | (excess) |
| Example 10 | batch | Me | 1.5 eq | TOL | 5 times | TBA | 2.6 eq | $Pd_2(dba)_3$•$CHCl_3$ | 0.05 eq | dtbpf | 0.20 eq | (excess) |
| Example 11 | batch | Me | 1.5 eq | MIBK | 5 times | TBA | 2.6 eq | $Pd_2(dba)_3$•$CHCl_3$ | 0.05 eq | dtbpf | 0.20 eq | (excess) |
| Example 12 | batch | Me | 1.5 eq | ACE | 5 times | TBA | 2.6 eq | $Pd_2(dba)_3$•$CHCl_3$ | 0.05 eq | dtbpf | 0.20 eq | (excess) |
| Example 13 | batch | Me | 1.5 eq | DMA | 33 times | TBA | 2.6 eq | $Pd_2(dba)_3$•$CHCl_3$ | 0.05 eq | dtbpf | 0.20 eq | (excess) |
| Example 14 | batch | Me | 1.1 eq | DMA | 24 times | TBA | 2.1 eq | $Pd_2(dba)_3$•$CHCl_3$ | 0.05 eq | dtbpf | 0.20 eq | (excess) |
| Example 15 | batch | Me | 1.5 eq | DMA | 33 times | TBA | 2.6 eq | $Pd_2(dba)_3$•$CHCl_3$ | 0.05 eq | dtbpf | 0.20 eq | (excess) |
| Example 16 | batch | Me | 1.5 eq | DMA | 33 times | TBA | 2.6 eq | $Pd_2(dba)_3$•$CHCl_3$ | 0.05 eq | amphos | 0.20 eq | (excess) |
| Example 17 | batch | Me | 1.5 eq | DMA | 33 times | TBA | 2.6 eq | $PdCl_2(dtbpf)$ | 0.10 eq | — | — | (excess) |
| Example 18 | batch | Me | 1.5 eq | DMA | 33 times | TBA | 2.6 eq | $Pd_2(dba)_3$•$CHCl_3$ | 0.05 eq | dtbpf | 0.20 eq | (excess) |
| Example 19 | flow | Me | 1.5 eq | DMA | 33 times | TBA | 2.6 eq | $Pd_2(dba)_3$•$CHCl_3$ | 0.05 eq | dtbpf | 0.20 eq | 2.0 eq |
| Example 20 | flow | Me | 1.5 eq | DMA | 33 times | TBA | 2.6 eq | $Pd_2(dba)_3$•$CHCl_3$ | 0.05 eq | dtbpf | 0.20 eq | 2.0 eq |
| Example 21 | flow | Me | 1.5 eq | DMA | 33 times | TBA | 2.6 eq | $Pd_2(dba)_3$•$CHCl_3$ | 0.05 eq | dtbpf | 0.20 eq | 2.0 eq |
| Example 22 | flow | Me | 1.5 eq | DMA | 33 times | TBA | 2.6 eq | $Pd_2(dba)_3$•$CHCl_3$ | 0.05 eq | dtbpf | 0.20 eq | 2.0 eq |
| Example 23 | flow | Me | 1.5 eq | DMA | 33 times | TBA | 2.6 eq | $Pd_2(dba)_3$•$CHCl_3$ | 0.01 eq | dtbpf | 0.04 eq | 2.0 eq | tert-Bu: tert-butyl group
DMA: N,N-dimethylacetamide
DME: 1,2-dimethoxyethane
AcOiPr: isopropyl acetate
DMF: N,N-dimethylformamide
TOL: toluene
MIBK: methyl isobutyl ketone
ACE: acetone
DBU: 1,8-diazabicyclo[5.4.0]-7-undesen
DIPEA: N,N-diisopropylethylamine
NMI: N-methylimidazole
TBA: tributylamine
NMM: N-methylmorpholine
$Pd_2(dba)_3$•$CHCl_3$: tris(dibenzylideneacetone)dipalladium (0) chloroform adduct
$PdCl_2(dtbpf)$: [1,1-bis(di-tert-butylphosphino)ferrocene]palladium(II) dichloride
dtbpf: 1,1'-bis(di-tert-butylphosphino)ferrocene
amphos: (4-dimethylaminophenyl)di-tert-butylphosphine

TABLE 2

| | Feeding rate of the raw material solution | Feeding rate of the carbon monoxide | Inner diameter of the T-shape mixer | Reaction temperature | Reaction pressure | Reaction time (Retention time) | Conversion rate | Yield |
|---|---|---|---|---|---|---|---|---|
| Example 1 | — | — | — | 80° C. | 0 MpaG | 5 hr | 99.4% | — |
| Example 2 | — | — | — | 80° C. | 0 MpaG | 5 hr | 98.7% | — |
| Example 3 | — | — | — | 80° C. | 0 MpaG | 6 hr | 100% | — |
| Example 4 | — | — | — | 80° C. | 0 MpaG | 6 hr | 36.9% | — |
| Example 5 | — | — | — | 80° C. | 0 MpaG | 2 hr | 100% | — |
| Example 6 | — | — | — | 80° C. | 0 MpaG | 5 hr | 81.7% | — |
| Example 7 | — | — | — | 80° C. | 0 MpaG | 2 hr | 46.1% | — |
| Example 8 | — | — | — | 80° C. | 0 MpaG | 2 hr | 41.4% | — |
| Example 9 | — | — | — | 80° C. | 0 MpaG | 2 hr | 78.7% | — |
| Example 10 | — | — | — | 80° C. | 0 MpaG | 2 hr | 44.6% | — |
| Example 11 | — | — | — | 80° C. | 0 MpaG | 2 hr | 52.8% | — |
| Example 12 | — | — | — | 56° C. | 0 MpaG | 7 hr | 39.8% | — |
| Example 13 | — | — | — | 80° C. | 0 MpaG | 7 hr | 100% | — |
| Example 14 | — | — | — | 80° C. | 0 MpaG | 7 hr | 100% | — |
| Example 15 | — | — | — | 80° C. | 0 MpaG | 7 hr | 99.6% | 86% |
| Example 16 | — | — | — | 80° C. | 0 MpaG | 6 hr | 99.5% | — |
| Example 17 | — | — | — | 80° C. | 0 MpaG | 7 hr | 77.2% | — |
| Example 18 | — | — | — | 100° C. | 0 MpaG | 6 hr | 60.7% | — |
| Example 19 | 0.4 mL/min | 2.0 mL/min | 2 mm | 120° C. | 0.6 MpaG | 0.8 hr | 99.0% | 84% |
| Example 20 | 0.1 mL/min | 0.5 mL/min | 2 mm | 80° C. | 0 MpaG | 0.8 hr | 38.5% | — |
| Example 21 | 0.1 mL/min | 0.5 mL/min | 2 mm | 100° C. | 0 MpaG | 0.8 hr | 55.4% | — |
| Example 22 | 0.1 mL/min | 0.5 mL/min | 2 mm | 120° C. | 0 MpaG | 0.8 hr | 60.2% | — |
| Example 23 | 0.5 mL/min | 2.6 mL/min | 1.3 mm | 120° C. | 1.4 MpaG | 0.8 hr | 81.1% | 66% |

Example 24

Production of Vadadustat Intermediate (4x)
(without Aftertreatment of Vadadustat Intermediate (3x))

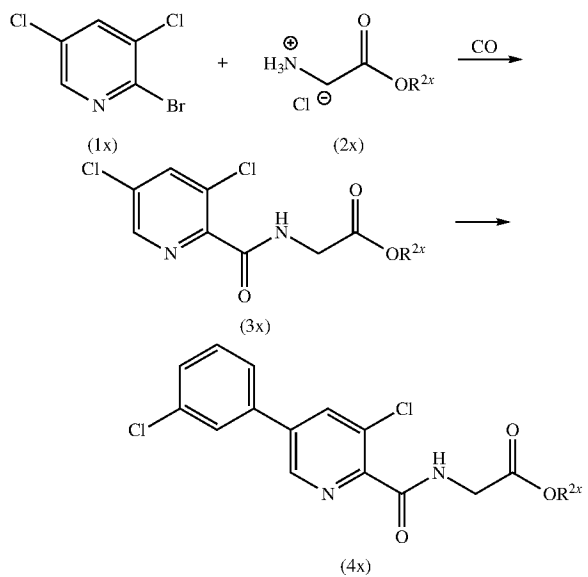

Into a reaction vessel were placed 0.50 g (2.2 mmol) of 2-Bromo-3,5-dichloropyridine (1x), 0.42 g (3.3 mmol, 1.5 eq) of glycine ester hydrochloride (2x) ($R^{2x}$=methyl group (Me)), 2.50 g (5 times the mass of (1x)) of dimethylacetamide, and 1.06 g (5.7 mmol, 2.6 eq) of tributylamine in this order, and then, degassing under reduced pressure and replacement by nitrogen were performed three times. Next, 0.11 g (0.11 mmol, 0.05 eq) of $Pd_2(dba)_3 \cdot CHCl_3$ and 0.21 g (0.44 mmol, 0.20 eq) of dtbpf were added thereto, and then, degassing under reduced pressure and replacement by nitrogen were performed three times. Subsequently, degassing under reduced pressure and replacement by carbon monoxide were performed three times, and then the mixture was reacted at 80° C. under normal pressure (0 MPaG) for 2 hours to produce a vadadustat intermediate (3x). The obtained reaction solution was analyzed, and the conversion rate was found to be 100%.

Conversion rate=Production amount (mol) of compound (3x)/(Production amount (mol) of compound (3x)+Remaining amount (mol) of compound (1x))×100(%)

To the reaction solution containing the vadadustat intermediate (3x) obtained above were added 0.38 g (2.4 mmol, 1.1 eq) of 3-chlorophenylboronic acid. 0.41 g (3.0 mmol, 1.4 eq) of potassium carbonate, 0.11 g (0.11 mmol, 0.05 eq) of $Pd_2(dba)_3 \cdot CHCl_3$, and 0.21 g (0.44 mmol, 0.20 eq) of dtbpf, and degassing under reduced pressure and replacement by nitrogen were performed three times. Then, the resulting mixture was reacted at 100° C. for 24 hours to produce a second vadadustat intermediate (4x). The obtained reaction solution was analyzed, and the conversion rate was found to be 86.3%.

Conversion rate = Production amount (mol) of compound (4x)/(Production amount (mol) of compound (4x) + Remaining amount (mol) of compound (3x))×100(%)

REFERENCE SIGNS LIST

1a: Carbon monoxide feeding unit
1b: Raw material solution feeding unit
2: Mixing unit
3: Tubular reactor unit
4: Mass flow controller 5: Metering pump
6: Back pressure valve
7: Temperature control device
8: Vessel

The invention claimed is:

1. A method for producing a first vadadustat intermediate comprising:

reacting a compound represented by the following formula (1):

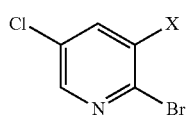

wherein X represents a chlorine atom, a hydroxy group, or $OP^1$; and $P^1$ represents an oxygen protecting group, with glycine or a glycine derivative represented by the following formula (2):

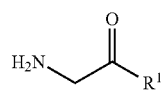

wherein $R^1$ represents a hydroxy group, $OR^2$, or $NR^3R^4$; $R^2$, $R^3$, and $R^4$ independently represent an alkyl group having 1 to 20 carbon atoms and optionally having a substituent, an aryl group having 6 to 20 carbon atoms and optionally having a substituent, or an aralkyl group having 7 to 20 carbon atoms and optionally having a substituent; and $R^3$ and $R^4$ may join together to form a ring, or a salt of the glycine or the glycine derivative in the presence of carbon monoxide to produce the first vadadustat intermediate represented by the following formula (3):

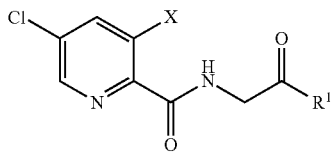

wherein $R^1$ and X are the same as the above.

2. The method for producing the first vadadustat intermediate according to claim 1, wherein the reaction of the compound represented by the formula (1) with the glycine or the glycine derivative represented by the formula (2), or the salt of the glycine or the glycine derivative is performed in the presence of a metal catalyst.

3. The method for producing the first vadadustat intermediate according to claim 2, wherein the metal catalyst is a catalyst containing Pd.

4. The method for producing the first vadadustat intermediate according to claim 1, wherein the reaction of the compound represented by the formula (1) with the glycine or the glycine derivative represented by the formula (2), or the salt of the glycine or the glycine derivative is performed in a flow reactor.

5. The method for producing the first vadadustat intermediate according to claim 4, wherein the reaction in the flow reactor is performed at 60° C. or higher.

6. The method for producing the first vadadustat intermediate according to claim 4, wherein the reaction in the flow reactor is performed under a pressurized condition of a gauge pressure of 0.1 MPa or more.

7. A method for producing a second vadadustat intermediate comprising:

producing the first vadadustat intermediate represented by the formula (3) by the method according to claim 1; and reacting, subsequently without aftertreatment, a reaction solution containing the obtained first vadadustat intermediate with 3-chlorophenylboronic acid to produce the second vadadustat intermediate represented by the following formula (4):

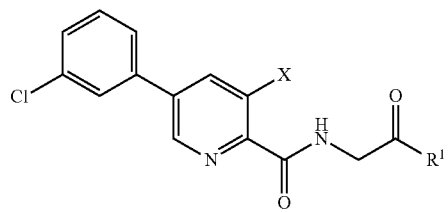

wherein $R^1$ and X are the same as the above.

8. The method for producing the first vadadustat intermediate according to claim 2, wherein the reaction of the compound represented by the formula (1) with the glycine or the glycine derivative represented by the formula (2), or the salt of the glycine or the glycine derivative is performed in a flow reactor.

9. The method for producing the first vadadustat intermediate according to claim 8, wherein, in the reaction performed in the flow reactor, the amount of the metal catalyst used is 0.05 mol or less per mole of the compound represented by the formula (1).

* * * * *